United States Patent [19]

Cook et al.

[11] 4,391,143
[45] Jul. 5, 1983

[54] ULTRASONIC PROBE FOR INSPECTING DOUBLE-WALL TUBE

[75] Inventors: Kenneth V. Cook, Clinton; Robert A. Cunningham, Jr., Powell; Horace T. Murrin, Alcoa, all of Tenn.

[73] Assignee: The United States of America as represented by the United States Department of Energy, Washington, D.C.

[21] Appl. No.: 268,424

[22] Filed: May 29, 1981

[51] Int. Cl.³ .................. A61B 5/04; G01N 29/00; G01M 7/00
[52] U.S. Cl. ............................ 73/623; 73/588; 310/335
[58] Field of Search .......... 73/642, 623, 632, 588; 310/334, 335, 348

[56] References Cited

U.S. PATENT DOCUMENTS

| | | | |
|---|---|---|---|
| 2,785,308 | 3/1957 | Stahl | 310/348 |
| 3,168,659 | 2/1965 | Bayre | 73/642 |
| 3,371,660 | 3/1968 | Carlin | 310/334 |
| 4,037,465 | 7/1977 | Cook et al. | 73/623 |
| 4,059,989 | 11/1977 | Halsey | 73/620 X |
| 4,073,193 | 2/1978 | Mastandrea | 310/334 |
| 4,089,227 | 5/1978 | Falgari et al. | 73/623 |
| 4,101,865 | 7/1978 | Schurr | 310/334 |
| 4,192,977 | 3/1980 | Stamm | 73/632 |
| 4,325,258 | 4/1982 | Foster | 310/334 |

*Primary Examiner*—Anthony V. Ciarlante
*Assistant Examiner*—David V. Carlson

[57] ABSTRACT

An ultrasonic probe for inspecting the interface between the walls of a double-wall tube comprises a cylindrical body member having two cavities axially spaced apart thereon. The probe is placed in the tube and ultrasonic energy is transmitted from a transducer in its body member to a reflector in one of its cavities and thence into the inner wall of the tube. A second transducer in the probe body member communicates with the second cavity through a collimation passage in the body member, and the amount of ultrasonic energy reflected from the interface between the walls of the tube to a second reflector through the collimation passage to the second transducer depends upon the characteristics of said interface.

2 Claims, 2 Drawing Figures

ULTRASONIC PROBE FOR INSPECTING DOUBLE-WALL TUBE

BACKGROUND OF THE INVENTION

This invention resulted from a contract with the United States Department of Energy and relates to an inspection device. More particularly, the invention relates to an ultrasonic probe placed in a double-wall tube to detect flaws at the interface between concentric walls thereof.

U.S. Pat. No. 4,037,465, issued on July 16, 1977, to K. Cook, D. Koerner, R. Conningham, Jr., and G. Murrin, Jr. (three of whom are co-inventors of the invention presented herein), discloses an ultrasonic probe which can be used to conveniently and effectively inspect a single-wall tube from the bore side thereof. However, for inspecting duplex (i.e., double-wall) tubes used in apparatus such as heat exchangers, the proper use of the inspection probe of the aforesaid patent require supplemental information to adjust both flaw detection and sensitivity. The supplemental information must elevate the interface for some reflection-transmission characteristics.

SUMMARY OF THE INVENTION

It is therefore an object of this invention to provide an improved ultrasonic probe for inspecting small diameter tubes from the interior thereof.

Another object of the invention is to provide an ultrasonic probe capable of determining sonic reflection-transmission characteristics of the interface between walls of a double-wall tube.

These objects and other advantages are attained by a preferred embodiment of the invention comprising a cylindrical body member sized to fit closely within the bore of a double-wall tube and moved therealong when in use. Two cavities extend inwardly from the periphery of the probe body member on one side thereof, these cavities being spaced apart axially of the body member and the portion of the latter disposed between the cavities constituting a baffle wall which blocks direct transmission of ultrasonic energy therebetween. Mounted within the probe body member is a first transducer which transmits ultrasonic energy into one of the aforesaid cavities (hereinafter referred to as the first cavity for convenience of identification). The first transducer is also operative to sense ultrasonic energy for a reason that will become apparent hereinafter. A first reflector is mounted within the first cavity and aligned with the first transducer so that it receives ultrasonic energy therefrom and directs it to the inner surface of the inspected tube at a predetermined angle. A second transducer is also mounted in the probe body member, this transducer being operative to sense ultrasonic energy and spaced from the other of the aforesaid cavities (hereinafter referred to as the second cavity) on the side thereof remote from the first cavity. A collimation passage is disposed within the probe body member and extends from the second cavity to the second transducer, and a second reflector is mounted within the second cavity and aligned with this passage. Ultrasonic energy emanating from the first transducer is reflected from the first reflector to the inner surface of the inspected tube, part of this energy entering the tube and part of the energy being reflected back to the first reflector and thence to the first transducer. The path traveled by energy that enters the inspected tube depends upon the characteristics of the interface between the two walls of the tube. If the walls of the tube are not bonded together, the ultrasonic energy will be reflected at the interface back to the inner surface of the tube and will pass into the second cavity, impinge on the second reflector therein, and then travel through the collimation passage to the second transducer. If there is a good bond between the wall of the inspected tube, sound energy will move into the outer wall of the tube and will reflect back at the outer surface thereof along a path that does not intersect the second reflector. The spatial arrangement of the second reflector, collimation passage, and second transducer ensures that only the ultrasonic energy reflected back from the interface between the tube walls is transmitted to the second transducer. The first and second transducers are connected to suitable electrical circuitry of the type described in U.S. Pat. No. 4,037,465, and this circuitry processes the electrical signals generated by impingement of ultrasonic energy on the transducers to provide an output indicative of the nature of the interface between the tube walls.

DETAILED DESCRIPTION OF THE PREFERRED EMBODIMENT

Figure 1:
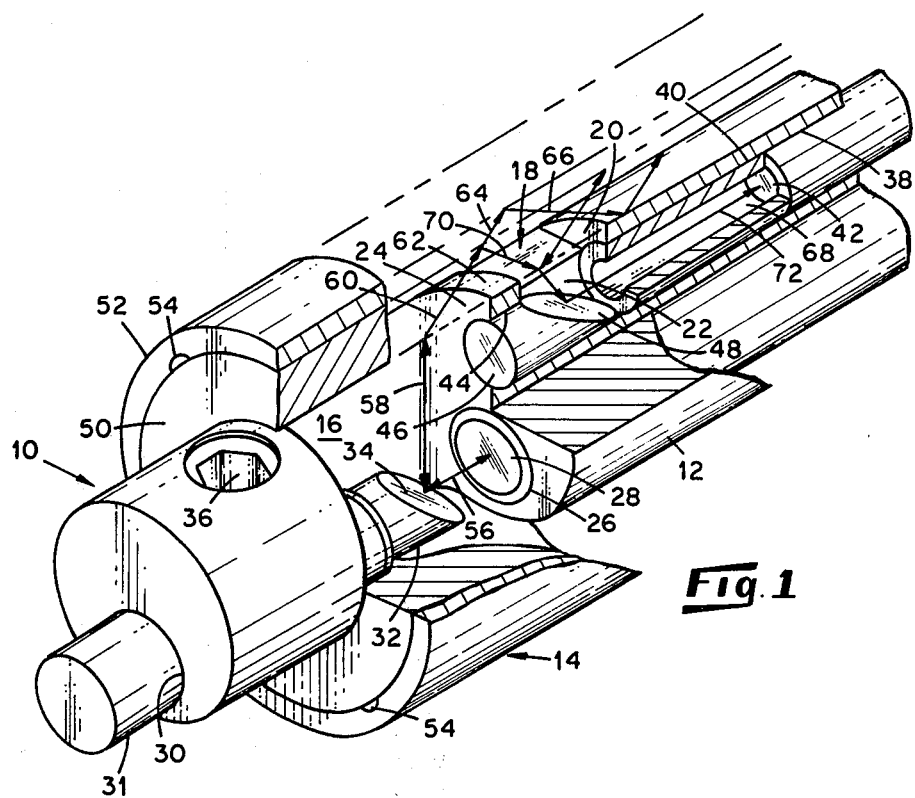
FIG. 1 is a pictorial view of a preferred ultrasonic probe embodiment of the invention, a cylindrical body member thereof being cut away in the drawing so that other components can be seen and the body member being illustrated within a double-wall tube (partially cut away and partially in phantom) of the type inspected by the probe.

In FIG. 1, reference number 10 generally designates an ultrasonic probe assembly constituting a preferred embodiment of this invention, the assembly comprising a cylindrical body member 12 sized to fit closely within the bore of a double-wall tube generally designated by reference number 14. Body member 12 is mounted on a suitable means (not shown) for moving it axially in tube 14 and simultaneously rotating it about its longitudinal axis. Body member 12 is provided with a first cavity 16 in the form of a deep notch extending transversely across the body member adjacent its free end (i.e., the left end of the body member in the drawing). Reference number 18 generally designates a second cavity which is aligned with and axially spaced from said first cavity 16 and which includes (1) an outer portion in the form of a shallow notch 20 extending transversely across body member 12 at an angle of 90° relative to the notch forming first cavity 16; and (2) a hemicylindrical recess 22 extending inwardly of the body member from the middle portion of notch 20. The portion 24 of body member 12 disposed between first cavity 16 and second cavity 18 constitutes a baffle wall which blocks the direct transmission of ultrasonic energy between the cavities.

Mounted in a first aperture 26 extending axially of body member 12 from the wall of first cavity 16 is a first transducer 28 operative to (1) transmit ultrasonic energy into the first cavity, and (2) sense ultrasonic energy and in response thereto, generate an analog electrical signal. A second aperture 30 extends axially of body member 12 from its forward end surface to fit cavity 16, this aperture being coaxial with aperture 26. A holder 31 for a cylindrical first reflector 32 having a flat reflector face 34 is slidably fitted in aperture 30 and held in a selected position therein by a set screw 36. The reflector face 34 of first reflector 30 is located in first cavity 16 and inclined at an angle of 55° relative to the longitudinal axis of body member 12.

Figure 2:
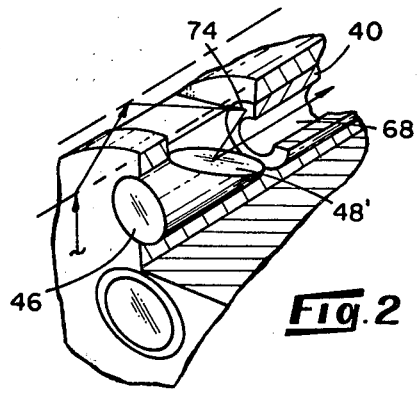
FIG. 2 is a detail view illustrating a modified arrangement of a component of the FIG. 1 embodiment.

A third aperture 38 extends axially of body member 12 from its rear end surface to second cavity 18, this aperture being coaxial with recess 22. A tubuar collimator insert 40 is mounted within aperture 38 with its forward end even with the rear wall of the notch portion of second cavity 18. Disposed within the bore of collimator insert 40 and spaced from second cavity 18 is a second transducer 42 operative to sense ultrasonic energy and in response thereto generate an analog electrical signal. Mounted in a fourth aperture 44 extending axially of body member 12 between first cavity 16 and recess 22 of second cavity 18 is a second cylindrical reflector 46 having a flat reflector face 48 located in the second cavity and inclined at an angle of 35° relative to the longitudinal axis of the body member 12. FIG. 2 illustrates a modification of the preferred embodiment of the invention wherein the reflector face 48' of reflectr 46 is inclined at an angle of 55° relative to the longitudinal axis of body member 12.

OPERATION OF THE EMBODIMENTS OF THE INVENTION

As mentioned hereinbefore, body member 12 is mounted on means which can move it along the bore of tube 14 and simultaneously rotate it about its longitudinal axis. It is necessary to connect first and second transducers 28,42 to electrical circuitry of the type described in U.S. Pat. No. 4,037,465, and as stated in the patent this can be accomplished by means of a suitable rotary joint coupled to body member 12.

Tube 14 comprises an inner wall 50, an outer wall 52, and a plurality of grooves 54 extending axially of the outer wall. Ultrasonic energy represented by line 56 in FIG. 1 is transmitted into first cavity 16 of body member 12 by first transducer 28, the direction of travel of this energy being indicated by the arrowhead on the left end of the line. This ultrasonic energy is deflected from the deflector face 34 of first reflector 32 to the inner surface of tube 14, as represented by line 58 and the uppermost arrowhead associated with the latter. Some of the ultrasonic energy impinging on tube 14 is reflected back to the reflector face 34 of first reflector 32 and travels therefrom back to first transducer 28 (as is also indicated by arrowheads associated with lines 56 and 58 in FIG. 1). Another portion of the ultrasonic energy enters the inner wall 50 of tube 14 and travels outwardy and rearwardly therein as represented by line 60. It should be noted here that the periphery 62 of the baffle wall portion 24 is preferably held against the inner surface of tube 14 by a biasing means of the type described and illustrated in U.S. Pat. No. 4,037,465, namely, a plurality of spring-loaded ball plungers identified by reference numbers 20,21 in the patent. Hence, ultrasonic energy cannot pass directly between first cavity 16 and second cavity 18. If there is a good bond between the inner and outer walls of tube 14, ultrasonic energy will readily pass into outer wall 52 (as represented by portion 64 of line 60). Ultrasonic energy which thus crosses the interface between the inner and outer walls of tube 14 will be deflected at the outer surface of the tube back toward body member 12 (as represented by line 66), but most of this energy will not enter second cavity 18 or impinge upon reflector face 48 of reflector 46 so as to be deflected into the collimation passage 68 in collimation insert 40. However, if there is a poor bond or a gap between the inner and outer walls 50,52 (as at the location of grooves 54), most of the ultrasonic energy is deflected back toward body member 12 at the interface between the walls (as represented by line 70), and some of this backwardly deflected energy passages into the water in second cavity 18 and is deflected from deflector face 48 of second deflector 46 through the collimation passage in collimator insert 40 to second transducer 42 (as represented by line 72).

By means of electrical circuitry of the tye disclosed in U.S. Pat. No. 4,037,465, the electrical signals induced in first transducer 28 and second transducer 42 can be processed to provide an output which varies in accordance with the characteristics of the interface between the inner and outer walls 50,52 of tube 14, which characteristics change the amount of ultrasonic energy which passes through the collimation passage in collimator insert 40 to transducer 42 as explained hereinbefore. In the probe assembly disclosed in the aforementioned patent, a transducer responsive to ultrasonic energy is located in a cavity corresponding to second cavity 18 of body member 12 described herein. The large amount of ultrasonic energy which is reflected through tube 14 and impinge on a transducer so located, creates excessive signal noise that may prevent detection of the reflected signal from the interface between walls 50,52. With the spatial arrangement of second cavity 18, second transducer 42, and collimation passage 68, only certain reflected ultrasonic energy reaches transducer 42 and the difference in the amount of energy which impinges upon this transducer because of the reflective properties of the interface between walls 50,52 can be detected.

In the embodiment of the invention illustrated in FIG. 2, the reflector face 48' of second reflector is inclined so as to reflect through collimation passage 68 ultrasonic energy that is reflected from the end surface 74 of collimator insert 40. This arrangement of reflector face 48' is highly selective regarding the ultrasonic energy allowed to reach second transducer 42 after being reflected from the interface between walls 50,52 of tube 14.

What is claimed is:

1. An ultrasonic probe assembly for inspecting a double-wall structure, comprising:
    a body member having first and second cavities extending inwardly from its periphery and spaced apart from each other axially of one side thereof, the portion of said body member disposed between said first and second cavities constituting a baffle wall blocking direct transmission of ultrasonic energy therebetween;
    a first transducer mounted within said body member and operative to (1) transmit ultrasonic energy into said first cavity and (2) sense ultrasonic energy;
    a first reflector mounted within said first cavity and aligned with said first transducer so as to receive ultrasonic energy therefrom and reflect it to said double-wall structure at a predetermined angle, said first reflector also receiving ultrasonic energy reflected back from said double-wall structure and reflecting it to said first transducer;
    a second transducer mounted within said body member and operative to sense ultrasonic energy, said second transducer being spaced from said second cavity on the side thereof remote from said first cavity;

an aperture in said body member extending from said second cavity to said second transducer;

a tubular collimator insert mounted within said aperture; and a second reflector mounted within said second cavity and arranged to receive ultrasonic energy reflected from the end of said collimator insert adjacent thereto and reflect it through said collimator insert to said second transducer.

2. The assembly of claim 1 wherein the reflection face of said second reflector is inclined at an angle of 55° relative to the longitudinal axis of said body member.

* * * * *